US009891186B2

United States Patent
Wang et al.

(10) Patent No.: US 9,891,186 B2
(45) Date of Patent: Feb. 13, 2018

(54) METHOD FOR ANALYZING ANALYTE CONCENTRATION IN A LIQUID SAMPLE

(71) Applicant: NATIONAL TSING HUA UNIVERSITY, Hsinchu (TW)

(72) Inventors: Yu-Lin Wang, Zhubei (TW); Chen-Pin Hsu, Taipei (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 14/870,563

(22) Filed: Sep. 30, 2015

(65) Prior Publication Data

US 2016/0282295 A1    Sep. 29, 2016

(30) Foreign Application Priority Data

Mar. 27, 2015  (TW) .............................. 104110033 A (51) Int. Cl.
    *G01N 27/327*    (2006.01)
(52) U.S. Cl.
    CPC ..... *G01N 27/3277* (2013.01); *G01N 27/3276* (2013.01)
(58) Field of Classification Search
    CPC ........ G01N 33/68; G01N 33/49; G01N 33/80; G01N 33/26; G01N 27/48; G01N 27/26; G01N 27/327; G01N 27/3272; C12Q 1/6813; C12Q 1/6876; C12Q 1/6825; C12Q 1/6869; C12Q 1/00; C12Q 1/02; C12Q 1/006; C12Q 1/34; C12Q 1/54; A61B 5/05; A61B 5/14532; A61B 5/14535
    See application file for complete search history.

(56) References Cited

U.S. PATENT DOCUMENTS

| | | | |
|---|---|---|---|
| 2002/0168652 A1* | 11/2002 | Werner | B01J 19/0046 435/6.12 |
| 2007/0074977 A1* | 4/2007 | Guo | A61B 5/14532 205/792 |
| 2007/0111202 A1* | 5/2007 | Henkens | C12Q 1/6825 435/5 |
| 2007/0235346 A1 | 10/2007 | Popovich et al. | |
| 2009/0288960 A1* | 11/2009 | Rubin | G01N 33/5438 205/777.5 |
| 2012/0037515 A1* | 2/2012 | Solanki | C12Q 1/6825 205/780.5 |
| 2014/0054170 A1* | 2/2014 | Tsukahara | G01N 27/327 204/403.01 |
| 2014/0087374 A1* | 3/2014 | Kayyem | B01L 3/5027 435/6.11 |
| 2014/0106441 A1* | 4/2014 | Wang | C12Q 1/689 435/287.2 |

FOREIGN PATENT DOCUMENTS

TW      I367325 A    7/2012
WO  WO 2013/048087 A2  4/2013

* cited by examiner

*Primary Examiner* — Gurpreet Kaur
(74) *Attorney, Agent, or Firm* — Birch, Stewart, Kolasch & Birch, LLP (57) ABSTRACT

A method for analyzing concentration of an analyte in a liquid sample applied to a biosensor includes: applying a voltage pulse to the liquid sample applied to the biosensor, the voltage pulse having a pulse width of not greater than $10^{-3}$ second; monitoring a response current, which is produced in response to the voltage pulse, within the pulse width via electrodes of the biosensor; and analyzing the response current that is correlated to the concentration of the analyte in the liquid sample.

14 Claims, 12 Drawing Sheets

FIG. 1

| applying a voltage pulse to the liquid sample applied to the biosensor, the voltage pulse having a pulse width of not greater than $10^{-3}$ second | 201 |
|---|---|
| monitoring a response current, which is produced in response to the voltage pulse, within the pulse width via electrodes of the biosensor | 202 |
| analyzing the response current that is correlated to the concentration of the analyte in the liquid sample | 203 |

METHOD FOR ANALYZING ANALYTE CONCENTRATION IN A LIQUID SAMPLE

CROSS-REFERENCE TO RELATED APPLICATION

This application claims priority of Taiwanese Patent Application No. 104110033, filed on Mar. 27, 2015.

FIELD

The disclosure relates to a biosensor, more particularly to a method for analyzing analyte concentration in a liquid sample applied to a biosensor.

BACKGROUND

Figure 1:
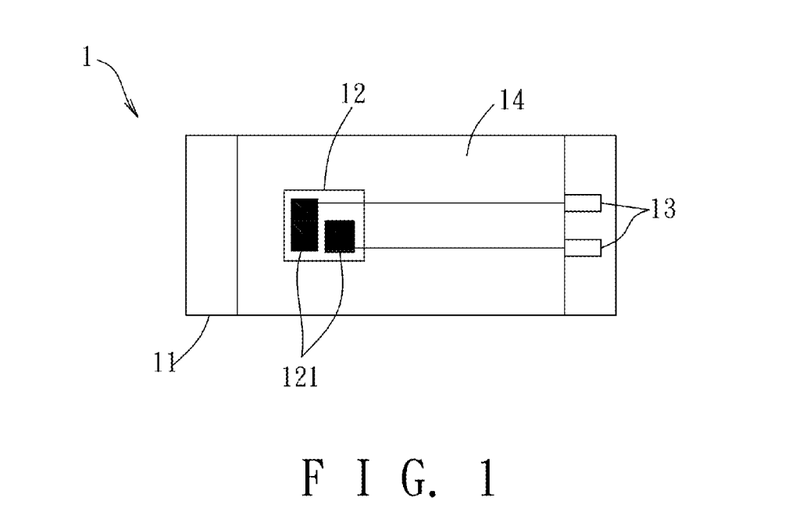
FIG. 1 is a schematic view of a conventional electrochemical biosensor.

Referring to FIG. 1, a conventional electrochemical biosensor 1 includes a substrate 11, a pair of sensing films 121 formed on the substrate 11, a pair of connecting terminals 13 respectively coupled to the sensing films 121, and an insulating layer 14 formed on the substrate 11 and defining a sensing window 12 for accessing the sensing films 121. A receptor, which can specifically bind to an analyte in a liquid sample, can be immobilized on the sensing films 121. By applying the liquid sample onto the sensing films 121 and applying a voltage between the sensing films 121 via the connecting terminals 13, a monitored steady state current can be utilized to detect the analyte concentration in the liquid sample. However, when the applied voltage is greater than a redox potential of the receptor, the receptor will lose its ability to perform specific binding with the analyte. Under such circumstance, a minimum amount of analytes in the liquid sample that can be detected by the biosensor (also known as the detection limit) is limited due to the limited amplitude of the applied voltage. Moreover, when analyte concentration variations between samples are relatively small, differences between the monitored steady state currents corresponding to the samples may not be large enough to be detected.

SUMMARY

An object of the disclosure is to provide a method which may alleviate at least one of the aforementioned drawbacks of the prior art.

Accordingly, one aspect of the present disclosure provides a method for analyzing concentration of an analyte in a liquid sample applied to a biosensor, including: applying a voltage pulse to the liquid sample applied to the biosensor, the voltage pulse having a pulse width of not greater than $10^{-3}$ second; monitoring a response current, which is produced in response to the voltage pulse, within the pulse width via electrodes of the biosensor; and analyzing the response current that is correlated to the concentration of the analyte in the liquid sample.

BRIEF DESCRIPTION OF THE DRAWINGS

Other features and advantages of the disclosure will become apparent in the following detailed description of the embodiments with reference to the accompanying drawings, of which:

FIGS. 5(B) and 5(C) are zoomed-in views of FIG. 5(A);

FIGS. 6(A) and 6(B) illustrate the response currents at 50 μs (i.e., the pulse width of the applied voltage pulse), where FIG. 6(A) illustrates the response currents of Examples 1 to 7 and Comparative Examples 1 to 3 and FIG. 6(B) illustrates the response currents of Examples 1 to 7 with respect to doxorubicin concentration in a logarithmic scale;

FIGS. 7(A) and 7 (B) shows the accumulated charges of the biosensor at 50 μs, where FIG. 7(A) illustrates the accumulated charges of Examples 1 to 7 and Comparative Examples 1 to 3, and FIG. 7(B) illustrates the accumulated charges of Examples 1 to 7 with respect to doxorubicin concentration in a logarithmic scale; and FIGS. 8(A) and 8(B) illustrate time constants with respect to different analyte concentrations at 50 μs, where FIG. 8(A) illustrates the time constants of Examples 1 to 7 and Comparative Examples 1 to 3, and FIG. 8(B) illustrates the time constant of Examples 1 to 7 with respect to doxorubicin concentration in a logarithmic scale.

DETAILED DESCRIPTION

Referring to FIGS. 2 to 8(B), the exemplary embodiment of a method for analyzing concentration of an analyte 251 in a liquid sample 25 applied to a biosensor 2 (see FIG. 3) includes Steps 201 to 203.

Figure 2:
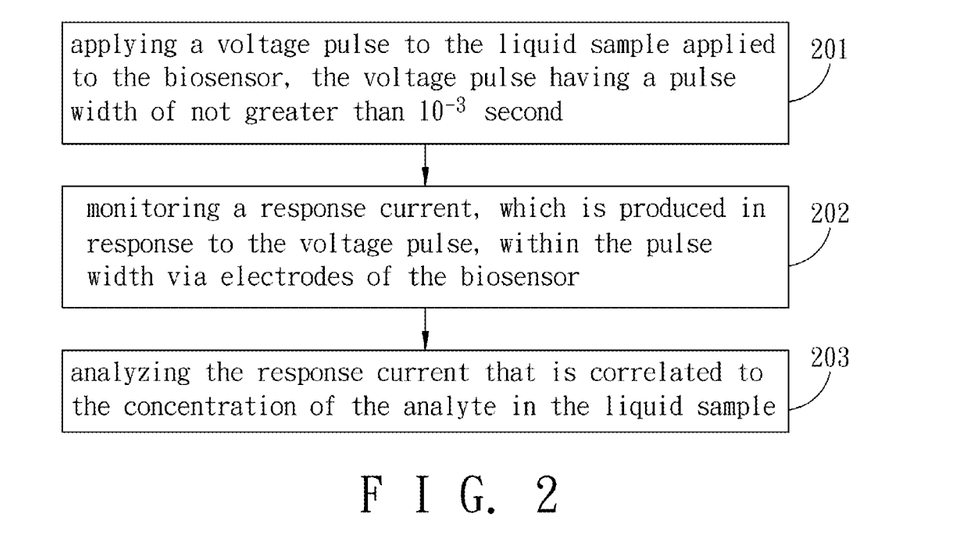
FIG. 2 is a flow chart illustrating an exemplary embodiment of a method for analyzing concentration of an analyte in a liquid sample according to the present disclosure.
Figure 3:
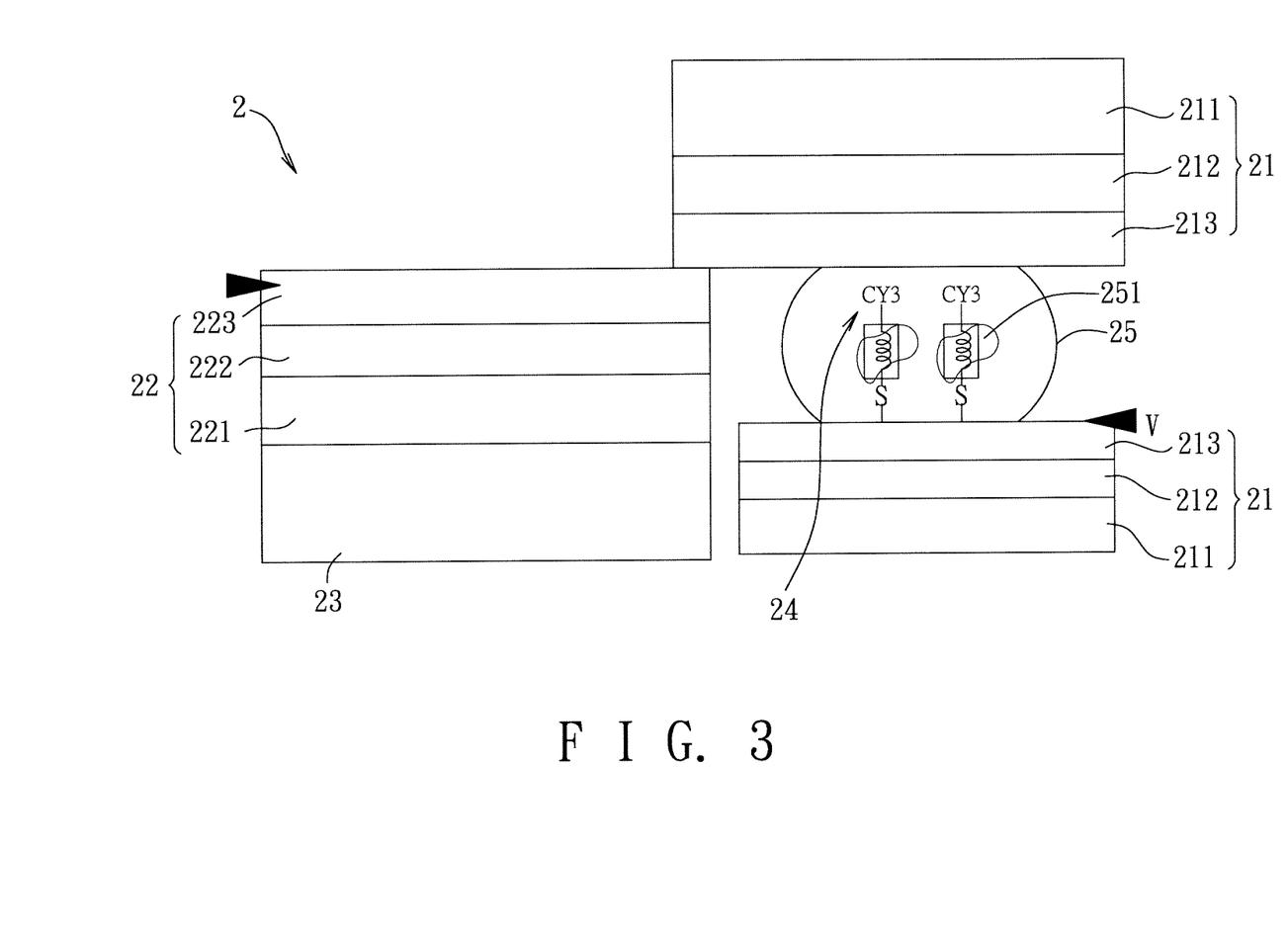
FIG. 3 is a schematic view of the exemplary embodiment illustrating a biosensor used in the method.

Step 201: applying a voltage pulse (V) to the liquid sample 25 which is applied to the biosensor 2 (see FIGS. 2 and 3).

As shown in FIG. 3, the biosensor 2 suitable for use in the method of this embodiment includes a pair of spaced-apart electrodes 21, each of which includes a silicon substrate 211, a silicon nitride ($Si_3N_4$) layer 212 that is formed on the silicon substrate 211, and a metal reactive layer 213 that is formed on the silicon nitride layer 212. The silicon nitride layer 212 serves as a dielectric layer to inhibit electron transport from the metal reactive layer 213 to the silicon substrate 211 so as to minimize sensing errors during measurement. In this embodiment, the metal reactive layer 213 is made of gold, but the metal reactive layer 213 may be made of other metals (e.g., platinum) or alloys having affinity to biological molecules and thus should not be limited to the disclosure of this embodiment. The metal reactive layer 213 of this embodiment may include gold nano-particles, which can be formed by chemical reduction, to further improve biological affinity of the electrodes 21. Since the technique of forming the gold nano-particles may be readily appreciated by those skilled in the art, further details will not be provided herein for the sake of brevity.

In this embodiment, as shown in FIG. 3, the metal reactive layers 213 of the electrodes 21 face each other. In greater detail, an auxiliary electrode 22 includes a silicon substrate 221 disposed on a glass substrate 23, a silicon nitride ($Si_3N_4$) layer 222 formed on top of the silicon substrate 221, and a metal reactive layer 223 formed on top of the silicon nitride layer 222 (i.e., having similar configuration as the electrodes 21). The total height of the auxiliary electrode 22 and the glass substrate 23 is greater than that of each electrode 21.

One of the electrodes 21 is disposed beside the auxiliary electrode 22 with the metal reactive layer 213 thereof facing upward. The other one of the electrodes 21 is disposed on top of the auxiliary electrode 22 with the metal reactive layer 213 thereof facing downward. A portion of the metal reactive layer 213 of the top one of the electrodes 21 physically and electrically contacts the metal reactive layer 223 of the auxiliary electrode 22, and a remaining portion of the metal reactive layer 213 faces and is spaced apart from the metal reactive layer 213 of the bottom one of the electrodes 21. In some embodiments, a distance between the metal reactive layers 213 of the electrodes 21 may be, but is not limited to, 200 μm. It should be noted that the structure of the electrodes 21 may be configured in a different manner in other embodiments (e.g., configured as a single metal piece instead of a multi-layer stacked structure). In addition, the configuration of the auxiliary electrode 22 may be different from that of the electrodes 21 in other embodiments of the present disclosure, so long as the auxiliary electrode 22 is electrically coupled to the top one of the electrodes 21.

Figure 4:
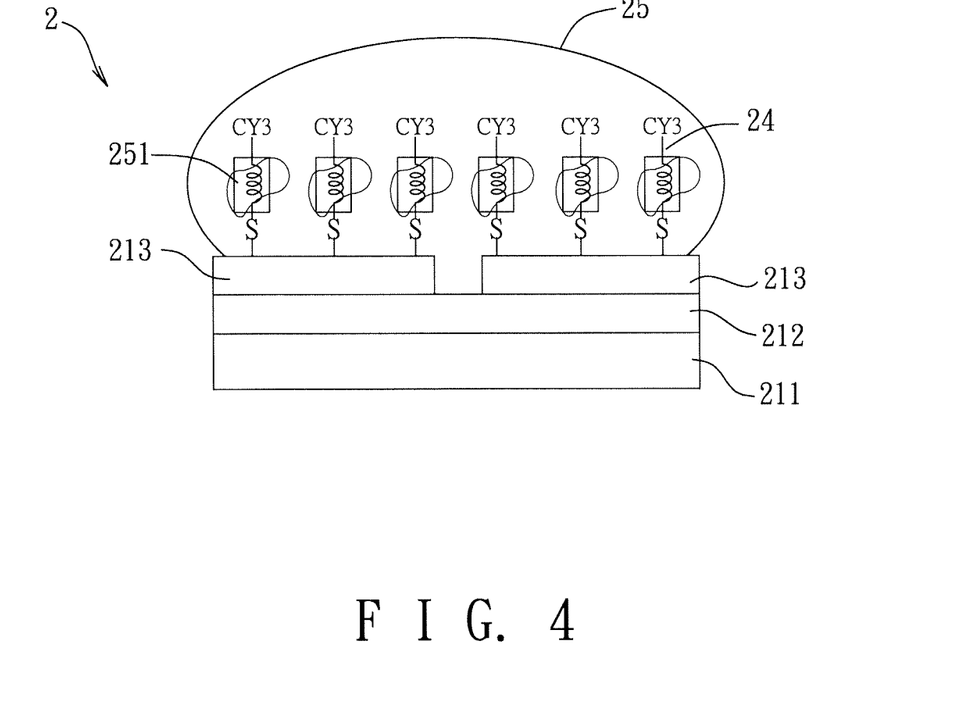
FIG. 4 is a schematic view of the exemplary embodiment, illustrating a modified biosensor used in the method.

In a variation of this embodiment, the biosensor 2 may be configured as illustrated in FIG. 4, where the metal reactive layers 213 of the electrodes 21 are arranged in a coplanar manner and the auxiliary electrode 22 is omitted. As shown in FIG. 4, the silicon substrates 211 of the electrodes 21, as well as the silicon nitride layers 212 thereof, are interconnected. In some embodiments, the metal reactive layer 213 of the electrodes 21 may be spaced apart from each other by a distance of about 25 μm, but the distance is not limited thereto according to the present disclosure.

As illustrated in FIG. 4, the metal reactive layer 213 of at least one of the electrodes 21 may have a receptor 24 immobilized thereon for specific binding of the analyte 251. For example, when the analyte 251 is a protein, such as HIV-1 reverse transcriptase (HIV-1 RT) protein, or a chemical compound, such as doxorubicin, the receptor 24 can include duplex deoxyribonucleic acid (dsDNA) molecules or proteins which can specifically bind to the analyte 251. It should be noted that there is no other limitation on the selected receptor 24, so long as the receptor 24 can be immobilized on the metal reactive layer 213 and facilitate specific binding with the analyte 251. In an embodiment where the metal reactive layer 213 of at least one of the electrodes 21 is immobilized with the receptor 24, the surface of the metal reactive layer 213 exposed from the receptor 24, may be blocked using a protein to promote the specific binding between the analyte 251 and the receptor 24. Such blocking may be conducted using a protein solution. The protein may be, but is not limited to, bovine serum albumin (BSA) or the like.

Prior to the application of the voltage pulse (V) in Step 201, the liquid sample 25 is applied into a gap between the metal reactive layers 213 of the electrodes 21 of the biosensor 2 of FIG. 3. The liquid sample 25 may be, but is not limited to, a buffer solution (e.g., tris-EDTA buffer) or a biological sample such as human blood, blood serum and blood plasma, etc. The analyte 251 in the liquid sample 25 may specifically bind to the receptor 24 after a short period of time, for instance, 20 minutes, depending on the specie thereof.

In Step 201 of this embodiment, the voltage pulse (V) is applied between the auxiliary electrode 22, which is electrically coupled to the top one of the electrodes 21, and the bottom one of the electrodes 21. The applied voltage pulse (V) has a pulse width that is not greater than $10^{-3}$ second.

Within such pulse width, the transient current response of the liquid sample 25 at the biosensor 2 does not reach a steady state. In some embodiments, the pulse width may range from 2 μs to 100 μs. In some embodiments, the pulse width may range from 30 μs to 60 μs. The applied voltage pulse (V) may have an amplitude that is not greater than a redox potential of the receptor 24. In this embodiment, the amplitude of the voltage pulse (V) is about 0.5 V. It is worth noting that Step 201 can be conducted by a meter, an analyzer, a voltage generator and the like, and the biosensor 2 of this embodiment may be incorporated into a sensor strip.

Step 202: monitoring a response current within the pulse width of the voltage pulse (V) via the electrodes 21 of the biosensor 2. The application of the voltage pulse (V) produces a response current between the electrodes 21 due to the capacitance effect. The response current may be monitored using a recorder or an analyzer, such as Agilent B1530A.

Step 203: analyzing the response current that is correlated to the concentration of the analyte 251 in the liquid sample 25. The monitored response current can be analyzed using any suitable means, such as computers, analyzers or the like.

In one variation of this embodiment, the method may further include a step of performing integration computational processing on the response current with respect to the pulse width in accordance with the following equation:

$$Q = I \times t$$

where a total charge (Q) accumulated on the electrodes 21 within the pulse width (t) can be calculated from the response current (I). Such parameter obtained by performing the aforesaid integration computational processing may serve as an alternative or additional analyzing factor for analyzing the concentration of the analyte 251 in the liquid sample 25.

A time constant (τ) may serve as another alternative or additional analyzing factor for analyzing the concentration of the analyte 251 in the liquid sample 25, and is represented by the following equation:

$$<\tau> = \int \frac{I(t)}{I_{peak}} dt$$

In other words, in a variation of the exemplary embodiment, the method may further include steps of performing arithmetic computational processing to divide entries of the response current by a maximum value ($I_{peak}$) thereof, and performing integration computational processing on results of the arithmetic computational processing with respect to the pulse width to obtain the time constant (τ).

By applying the voltage pulse (V), which has a pulse width of not greater than $10^{-3}$ second, to the liquid sample 25 applied to the biosensor 2 and analyzing the response current of the biosensor 2 within the pulse width of the voltage pulse (V), the concentration of the analyte 251 in the liquid sample 25 can be detected and determined. In addition, a relatively high detection sensitivity can be achieved while under application of the voltage pulse (V) having a relatively low amplitude.

The following examples are for illustrating the exemplary embodiment only and should not be construed as limiting the scope of the present disclosure.

EXAMPLES

<Immobilization of the Receptor>

2.5 μL of a tris-EDTA (TE) buffer solution (containing 30 mM of Tris-Acid, 3 mM of EDTA and 30 mM of NaCl), with a pH value of 8, was applied dropwise to the gap between the electrodes 21 of the biosensor 2 illustrated in FIG. 3. Thereafter, a voltage pulse having a pulse width of 50 μs and an amplitude of 0.5 V was applied to the bottom one of the electrodes 21 while the top one of the electrodes 21, as well as the auxiliary electrode 22 was grounded (i.e., applied between the electrodes 21). A first response current was measured accordingly from the grounded electrode 21. After removing the TE buffer solution, a $5 \times 10^{-6}$ M dsDNA solution containing duplex DNA molecules (i.e., the receptor 24) was applied dropwise onto the metal reactive layer 213 of the bottom one of the electrodes 21 and remained thereon for 24 hours at 25° C., allowing the duplex DNA molecules to be immobilized thereon. The duplex DNA molecules have sequences of 5'-TTT GCT TTT TCG TCG TTT GCT TTT CGT TTT-thiol-3' and 5'-(Cy3)-AAA ACG AAA AGC AAA CGA CGA AAA AGC AAA-3', respectively. Thereafter, the electrodes were rinsed twice using phosphate buffer (pH=8) to remove non-binding dsDNA molecules. The TE buffer solution was then applied to the gap between the electrodes 21 and the same voltage pulse was again applied between the electrodes 21 of the biosensor 2 to obtain a second response current. By comparing the first and second response currents, immobilization of the duplex DNA molecules on the metal reactive layer 213 can be ascertained.

Example 1

2.5 μL of a pH8.0 TE buffer solution (i.e., the liquid sample 25), containing doxorubicin (i.e., the analyte 251) at a concentration of 1 μM, was applied to the gap between the metal reactive layers 213 of the electrodes 21 for 20 minutes at 25° C. Thereafter, the biosensor was rinsed twice using the phosphate buffer to remove the non-binding doxorubicin, and the TE buffer was applied to the gap of the biosensor 2. A voltage pulse, having a pulse width of 50 μs and an amplitude of 0.5V, was applied to the bottom one of the electrodes 21 of the biosensor 2 by an analyzer (Model: B1530/B1500A, commercially available from Agilent), and the response current was then monitored by the analyzer from the top one of the electrodes 21 through the auxiliary electrode 22. The measured response current of Example 1 is illustrated in FIGS. 5(A) to 5(C) and 6(A) to 6(B).

Examples 2 to 7

The methods of Examples 2 to 7 were similar to that of Example 1, with the sole difference residing in that the liquid samples 25 of Examples 2 to 7 have doxorubicin concentrations of 10 pM, 100 pM, 1 nM, 10 nM, 100 nM and 1 μM, respectively. The measured response currents are illustrated in FIGS. 5(A) to 5(C) and 6(A) to 6(B).

Comparative Example 1

The method of Comparative Example 1 was similar to that of Example 1. The differences therebetween reside in that the liquid sample applied to the biosensor in the method of Comparative Example 1 is D.I. water with no doxorubicin contained therein, and that no duplex DNA molecules (i.e., the receptor) were immobilized either one of the metal reactive layers of the biosensor of Comparative Example 1. The monitored response current of Comparative Example 1 is illustrated in FIGS. 5(A) to 5(C) and 6(A) to 6(B).

Comparative Example 2

The method of Comparative Example 2 was similar to that of Comparative Example 1, with the only difference residing in that the liquid sample applied to the biosensor of Comparative Example 2 is a 30 mM TE buffer solution with no doxorubicin contained therein. The monitored response current of Comparative Example 2 is illustrated in FIGS. 5(A) to 5(C) and 6(A) to 6(B).

Comparative Example 3

The method of Comparative Example 3 was similar to that of Comparative Example 2, with only the difference residing in that the duplex DNA molecules are immobilized on one of the metal reactive layers to serve as the receptor in the biosensor of Comparative Example 3. The monitored response current of Comparative Example 3 is illustrated in FIGS. 5(A) to 5(C) and 6(A) to 6(B).

[Data Analysis]

Figure 5A:
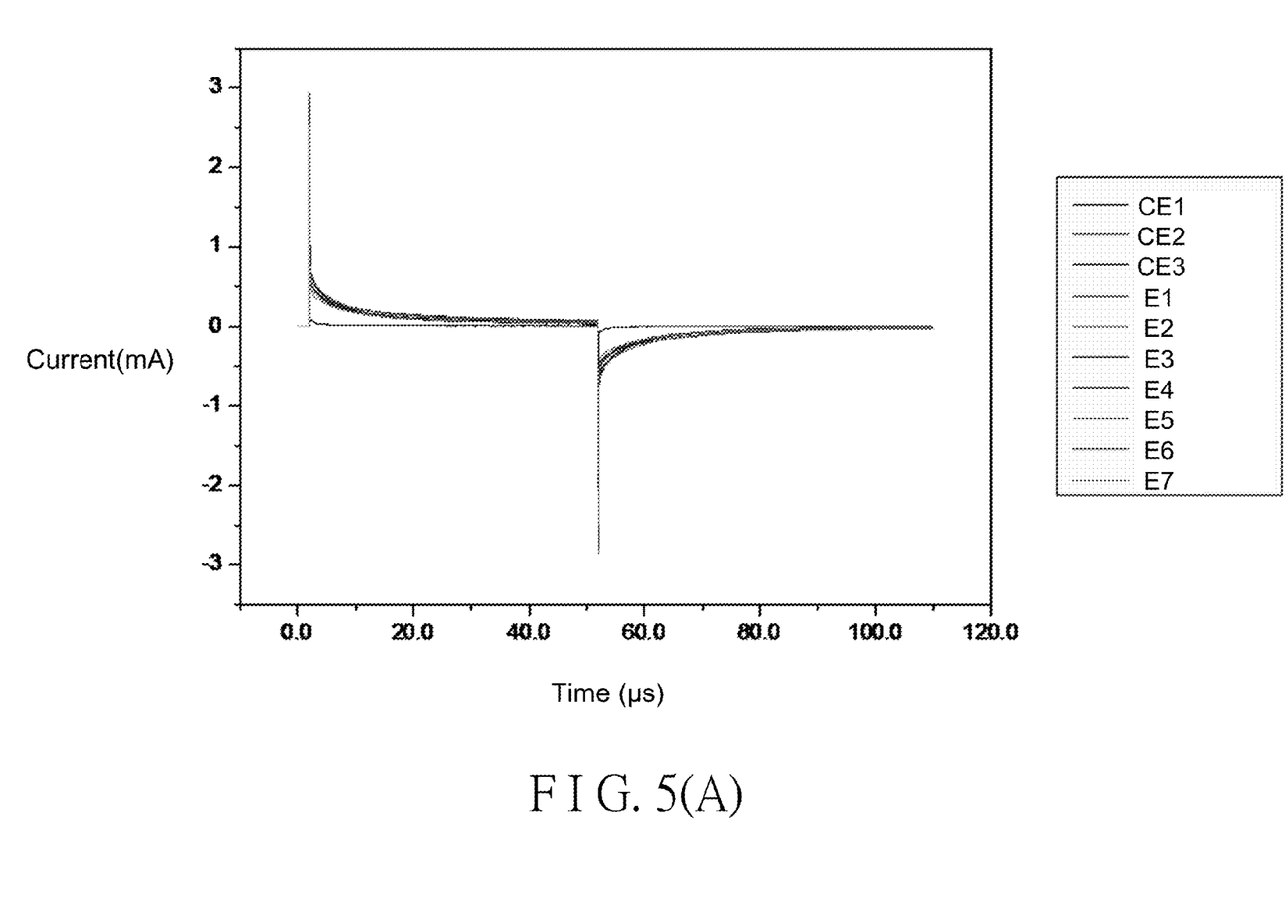
FIGS. 5(A) to 5(C) illustrate plots of response currents of Examples 1 to 7 and Comparative Examples 1 to 3 with respect to voltage applying time, where
Figure 5B:
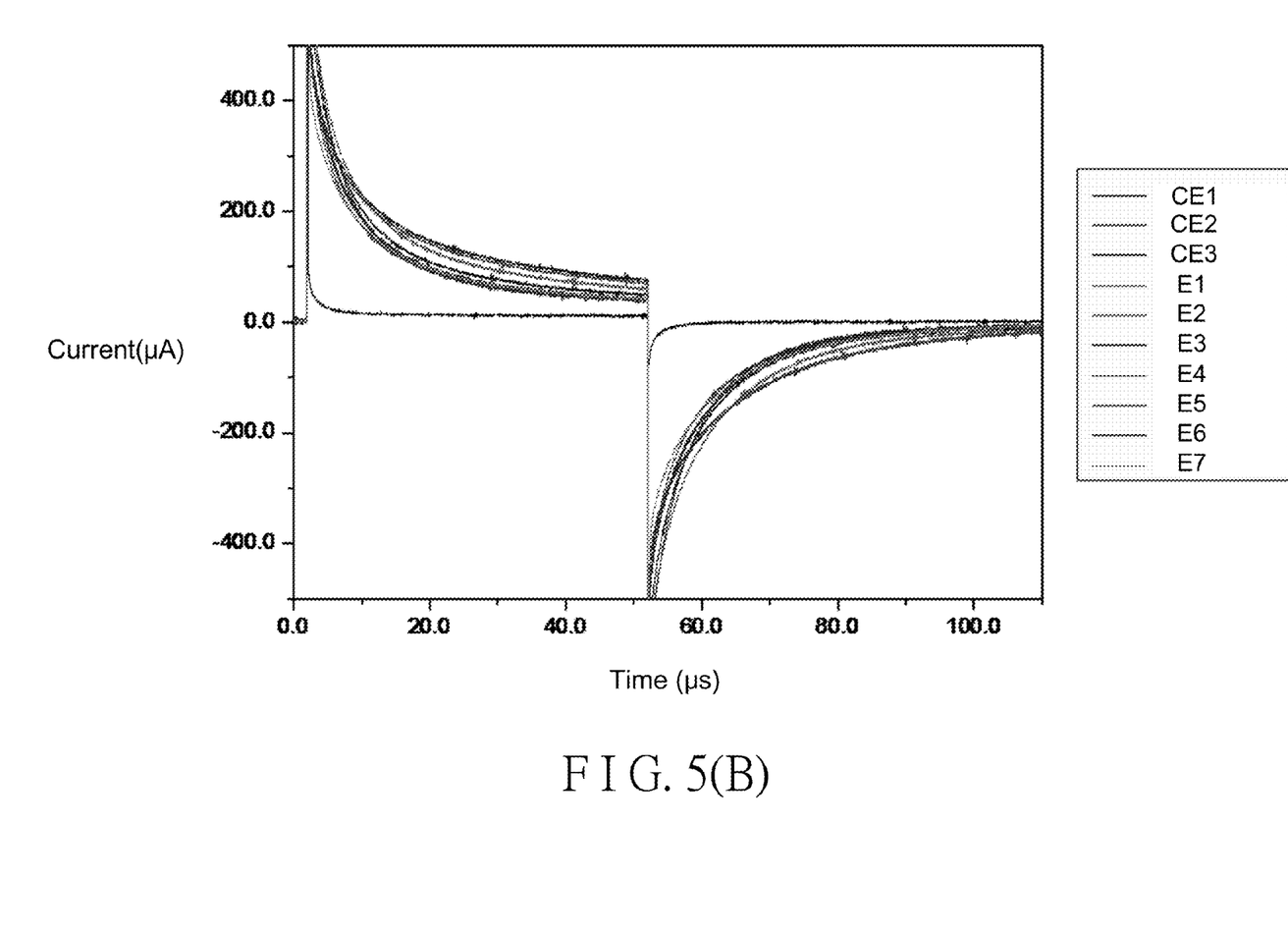
Figure 5C:
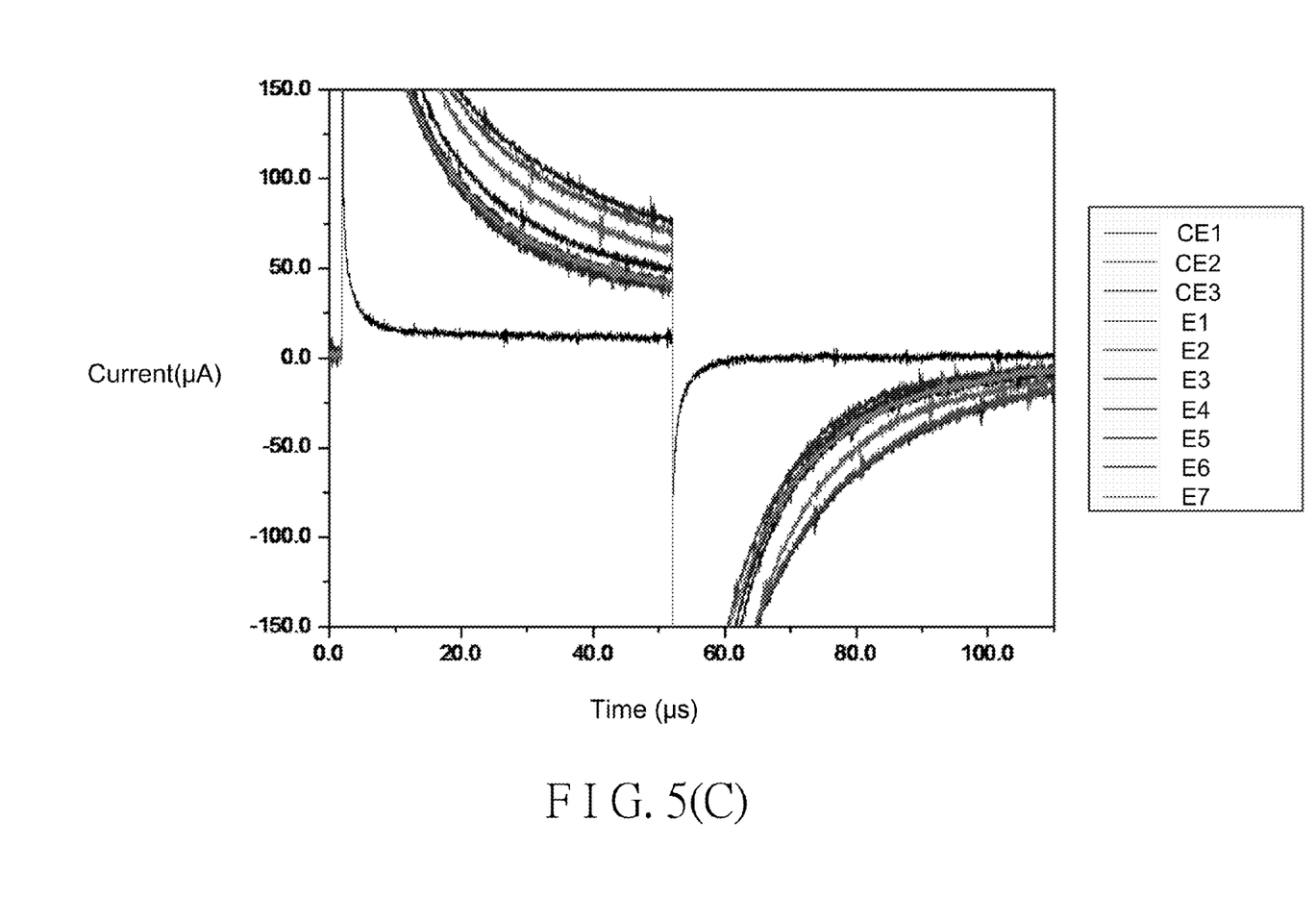
Figure 6A:
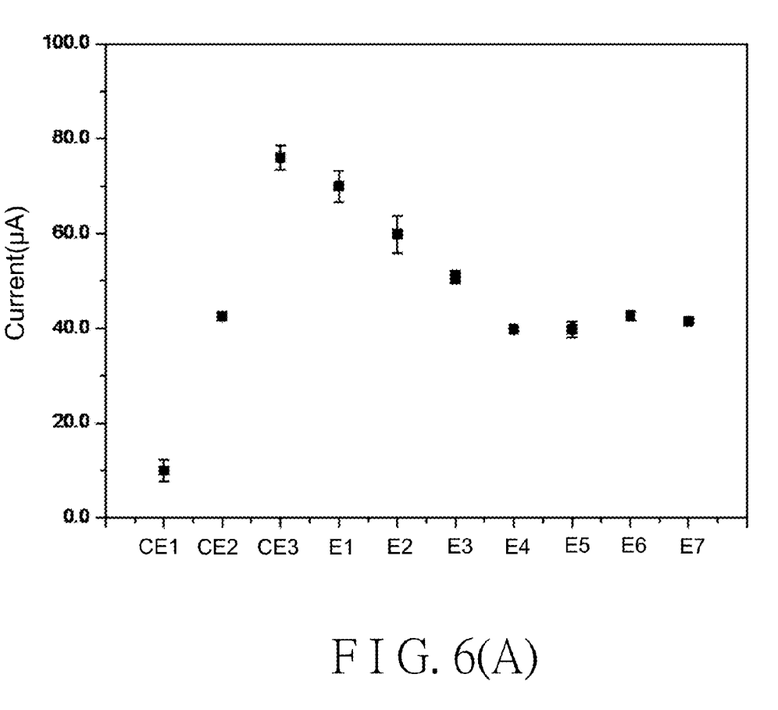
Figure 6B:
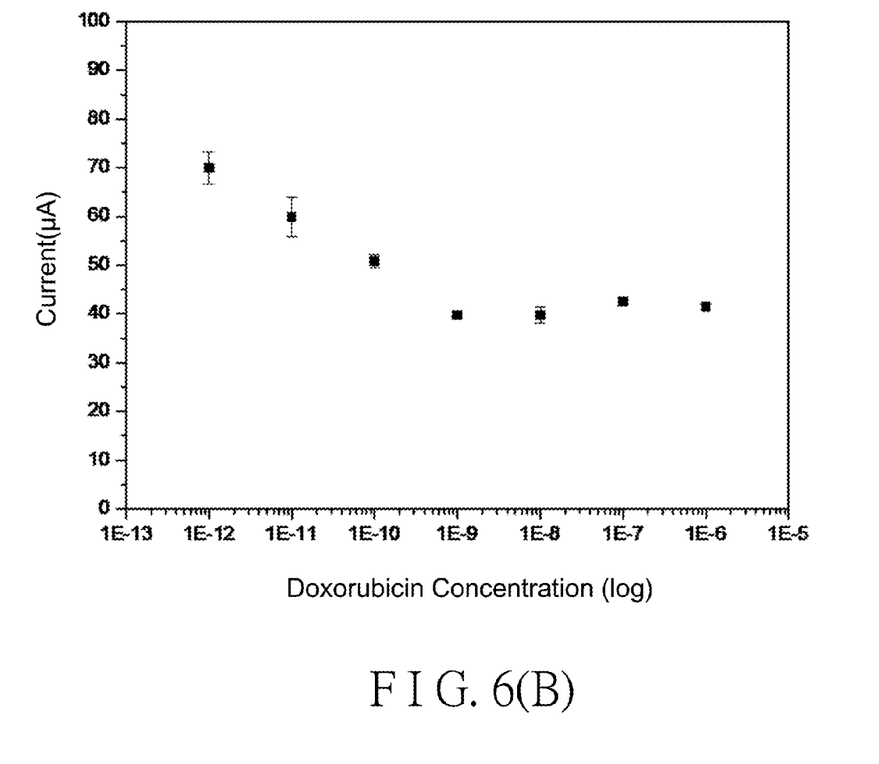

FIGS. 5(A) to 5(C) illustrate plots of the response currents of Examples 1 to 7 and Comparative Examples 1 to 3 with respect to the voltage pulse applying time, where FIGS. 5(B) and 5(C) are zoomed-in views of FIG. 5(A). It is clearly shown that the liquid samples with various analyte concentrations indeed have respective response currents under the same applied voltage pulse. In addition, with the increasing doxorubicin concentrations in the liquid samples, the response currents of Examples 1 to 4 tend to decrease accordingly. When the doxorubicin concentration goes beyond 10 nM (Examples 4 to 7), the receptor of the biosensor is saturated by doxorubicin. FIGS. 6(A) and 6(B), which illustrate the response currents of Examples 1 to 7 and Comparative Examples 1 to 3 at the pulse width of 50 μs (i.e., at 50 μs after the application of voltage pulse), further illustrates that the monitored response currents of Examples 1 to 4 are approximately in inverse proportion to the analyte concentration in the liquid samples. The results prove that the response current monitored within the pulse width of the voltage pulse is correlated to the analyte concentration in the liquid sample applied to the biosensor and can be utilized as a reliable analyzing factor.

Figure 7A:
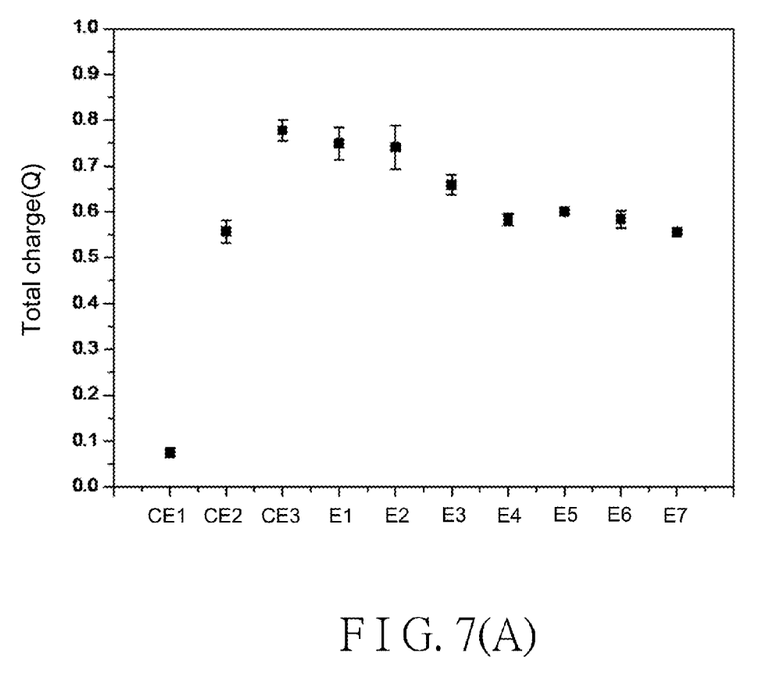
Figure 7B:
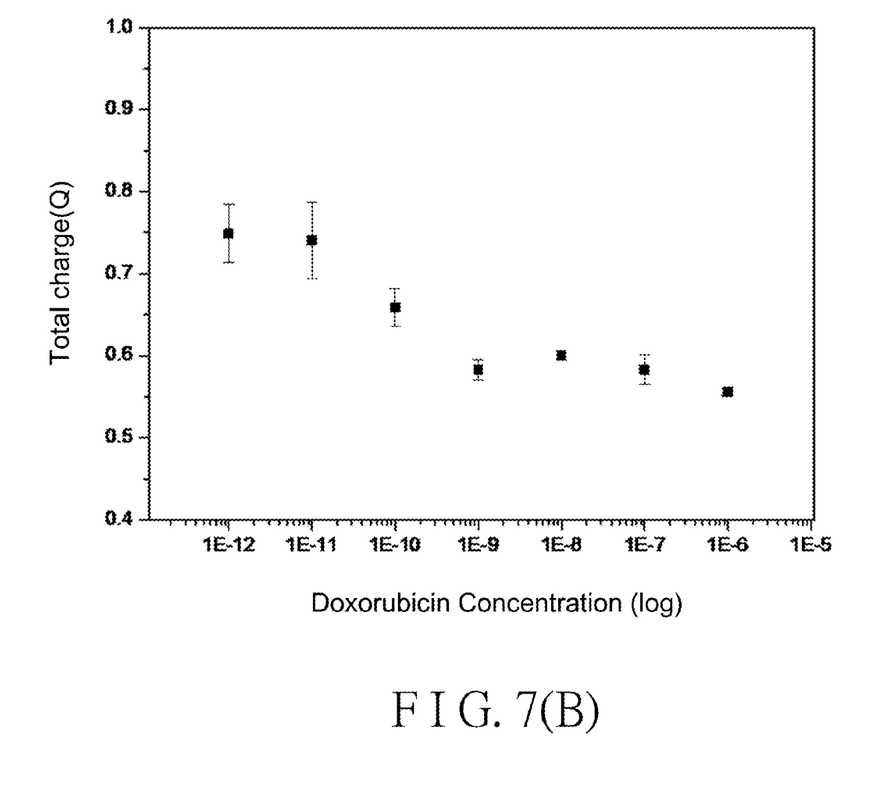
Figure 8A:
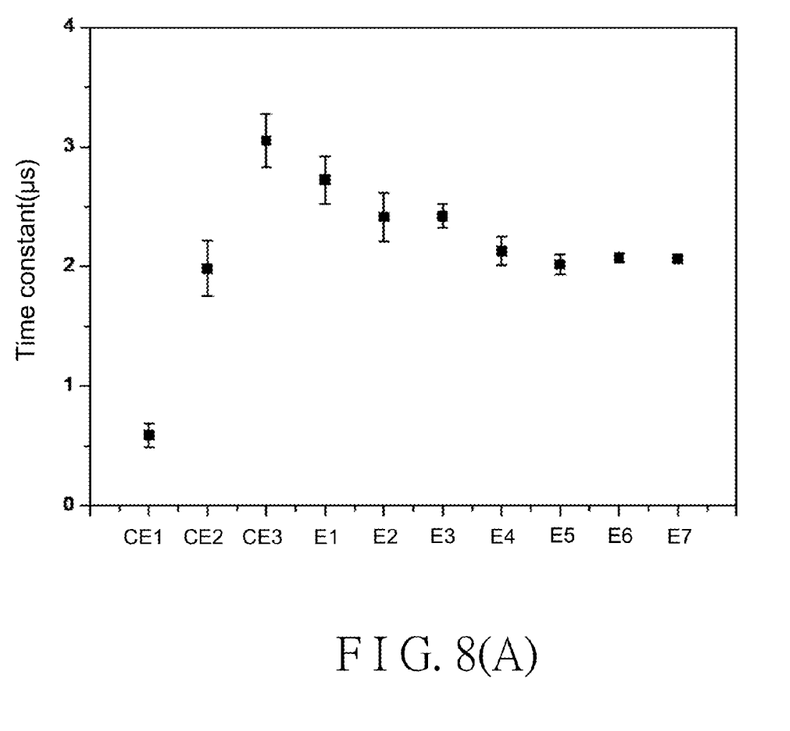
Figure 8B:
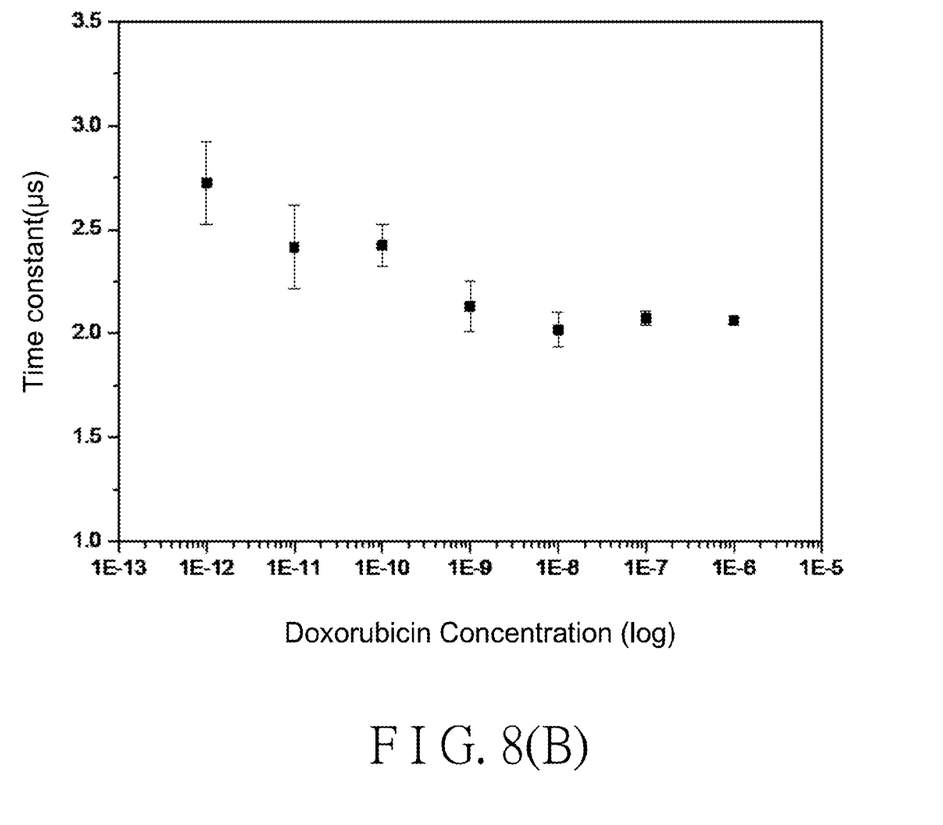

Integration computational processing on the response currents of Examples 1 to 7 and Comparative Examples 1 to 3 with respect to the pulse width was performed by the analyzer (Agilent B1530A) to obtain the amount of total charges accumulated at the biosensor, as illustrated in FIGS. 7(A) and 7(B). Similar to the response currents, it is shown that the amount of total charges accumulated at the biosensor is correlated to the analyte concentration in the liquid sample. As shown in FIGS. 7(A) and 7(B), the total accumulated charges of Examples 1 to 4 are approximately in inverse proportion to the doxorubicin concentration in the liquid sample and can be another reliable analyzing factor.

Arithmetic computational processing to divide entries of the response current of each of Examples 1 to 7 and Comparative Examples 1 to 3 by a maximum value of the monitored response current, and integration computational processing on results of the arithmetic computational processing with respect to the pulse width (50 μs) of the applied voltage pulse were performed to obtain a time constant (τ) for each of Examples 1 to 7 and Comparative Examples 1 to 3. As shown FIGS. 8(A) and 8(B), it is evident that the time constant is also correlated to the analyte concentration in the liquid sample and can be utilized as yet another reliable analyzing factor.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. A method for analyzing concentration of an analyte in a liquid sample applied to a biosensor, comprising:
    applying a voltage pulse to the liquid sample applied to the biosensor, the voltage pulse having a pulse width of not greater than $10^{-3}$ second;
    monitoring a response current, which is produced in response to the voltage pulse and between electrodes of the biosensor due to the capacitance effect, within the pulse width via the electrodes of the biosensor;
    analyzing the response current that is correlated to the concentration of the analyte in the liquid sample;
    performing integration computational processing on the response current with respect to the pulse width; and
    performing arithmetic computational processing to divide entries of the response current by a maximum value of the response current, and performing integration computational processing on results of the arithmetic computational processing with respect to the pulse width.

2. The method of claim 1, wherein the pulse width of voltage pulse ranges from 2 μs to 100 μs.

3. The method of claim 2, wherein the pulse width of the voltage pulse ranges from 30 μs to 60 μs.

4. The method of claim 1, wherein the electrodes of the biosensor include a pair of spaced-apart electrodes each having a metal reactive layer thereon, and the metal reactive layer of at least one of the electrodes has a receptor immobilized thereon for specific binding of the analyte.

5. The method of claim 4, wherein the metal reactive layer of each of the electrodes includes gold.

6. The method of claim 4, wherein the metal reactive layer of each of the electrodes includes gold nano-particles.

7. The method of claim 4, wherein the metal reactive layers of the electrodes face each other.

8. The method of claim 4, wherein the metal reactive layers of the electrodes are arranged in a coplanar manner.

9. The method of claim 4, wherein the receptor includes DNA.

10. The method of claim 9, wherein the receptor includes duplex DNA molecules.

11. The method of claim 9, wherein the receptor includes a protein.

12. The method of claim 4, wherein the analyte is a protein.

13. The method of claim 4, wherein the analyte is a chemical compound.

14. The method of claim 4, wherein the biosensor further comprises an auxiliary electrode having a metal reactive layer thereon, wherein one of the pair of spaced-apart electrodes is placed beside the auxiliary electrode with a portion of the metal reactive layer thereof physically and electrically contacting the metal reactive layer of the auxiliary electrode.

* * * * *